United States Patent [19]

Chupp

[11] 4,334,909
[45] Jun. 15, 1982

[54] N-(ALKOXYMETHYL)-2'-NITRO-6'-SUBSTITUTED-2-HALOACETANILIDES AND THEIR USE AS HERBICIDES AND PLANT GROWTH REGULANTS

[75] Inventor: John P. Chupp, Kirkwood, Mo.

[73] Assignee: Monsanto Company, St. Louis, Mo.

[21] Appl. No.: 133,761

[22] Filed: Mar. 25, 1980

[51] Int. Cl.³ ..................... A01N 37/22; C07C 103/32
[52] U.S. Cl. ......................................... 71/76; 71/118; 564/214
[58] Field of Search ................ 260/562 B; 71/118, 76; 564/214

[56] References Cited

U.S. PATENT DOCUMENTS

| | | | |
|---|---|---|---|
| 3,547,620 | 12/1970 | Olin | 71/118 |
| 3,642,895 | 2/1972 | Adams et al. | 260/562 B |
| 3,674,459 | 7/1972 | Alt | 71/118 |

*Primary Examiner*—Catherine L. Mills
*Attorney, Agent, or Firm*—Patricia A. Coburn; Howard C. Stanley

[57] ABSTRACT

N-(Alkoxymethyl)-2'-nitro-6'-substituted-2-haloacetanilide compounds have been found to be useful as herbicides and plant growth regulants. The compounds have the formula

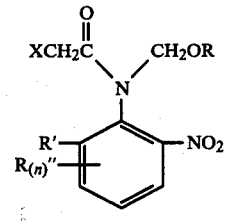

where X is chloro, bromo or iodo; R is $C_{1-5}$ alkyl, $C_{3-5}$ alkenyl, $C_{3-5}$ alkynyl or $C_{1-5}$ alkyl substituted by one to three $C_{1-5}$ alkoxy moieties, R' is hydrogen, $C_{1-5}$ alkyl, $C_{1-5}$ alkoxy, halogen or $NO_2$. R" is $C_{1-5}$ alkyl, $C_{1-5}$ alkoxy, halo, halo ($C_{1-5}$) alkyl or $NO_2$; n is zero, one or two.

33 Claims, No Drawings

N-(ALKOXYMETHYL)-2'-NITRO-6'-SUBSTITUTED-2-HALOACETANILIDES AND THEIR USE AS HERBICIDES AND PLANT GROWTH REGULANTS

This invention relates to certain N-(alkoxymethyl)-2'-nitro-6'-substituted-2-haloacetanilides compounds. The compounds of the invention have been found to be effective agricultural chemicals useful as herbicides as well as plant growth regulants.

The compounds of this invention are N-(alkoxymethyl)-2'-nitro-6'-substituted-2-haloacetanilides and may be represented by the formula

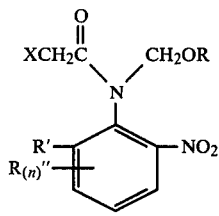

wherein X is chloro, bromo or iodo; R is $C_{1-5}$ alkyl, $C_{3-5}$ alkenyl, $C_{3-5}$ alkynyl or $C_{1-5}$ alkyl substituted by one to three $C_{1-5}$ alkoxy moieties; R' is hydrogen, $C_{1-5}$ alkyl, $C_{1-5}$ alkoxy, halogen or $NO_2$; R" is $C_{1-5}$ alkyl, $C_{1-5}$ alkoxyl, halo, halo ($C_{1-5}$) alkyl, or $NO_2$; n is zero, one or two.

The term "alkyl" and "alkoxy" refers to straight chain or branched chain alkyl and alkoxy groups. Illustrative of such alkyl groups are methyl, ethyl, n-propyl, isopropyl, n-butyl, tert-butyl, isobutyl, n-pentyl and the like. Illustrative of the term "alkoxy" is methoxy, ethoxy, isopropoxy, n-propoxy, n-butoxy, tert-butoxy, isobutoxy, pentoxy, and the like.

Alkyl substituted by one to three alkoxy moieties refers to such groups as methoxyethyl, ethoxyethyl, dimethoxyethyl, n-propoxymethyl, 2-ethoxypropyl, 4-isopropoxypropyl and the like.

"Haloalkyl" refers to such groups as, e.g., chloromethyl, bromomethyl, dichloromethyl, 2-dichloroethyl, trifluoromethyl, trichloromethyl, 2-trichloroethyl, 3-chloropropyl, and the like.

The term "alkenyl" refers to both straight chain and branched chain alkenyl groups containing 3–5 carbon atoms of the type $—C_nH_{2n-1}$.

The term "alkynyl" refers herein to an alkynyl group containing 3 to 5 carbon atoms of the type $—C_nH_{2n-3}$ and includes both straight chain and branched chain groups such as $—C{\equiv}CH$, $—CH_2C{\equiv}CH$, $—CH_2CH_2C{\equiv}CH$,

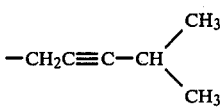

and the like.

The term "halogen" or "halo" as used herein includes chloro, bromo, fluoro and iodo atoms. The preferred halogen for use in this invention is chloro.

Non-limiting examples of the compounds of the present invention are:

2-chloro-2',6'-dinitro-N-(n-propoxymethyl)acetanilide;
2-chloro-2'-nitro-6'-methyl-N-(ethoxymethyl)acetanilide;
2-chloro-2'-nitro-N-(ethoxymethyl)acetanilide;
2-chloro-2'-nitro-N-(isobutoxymethyl)acetanilide;
2-chloro-2',6'-dinitro-N-(methoxymethyl)acetanilide;
2'bromo-2',6'-dinitro-N-(methoxymethyl)acetanilide;
2-bromo-2',6'-dinitro-N-(isopropoxymethyl)acetanilide;
2-iodo-2'-nitro-N-(methoxymethyl)acetanilide;
2-chloro-2'-nitro-6'-ethyl-N-(ethoxymethyl)acetanilide;
2-chloro-2'-nitro-6'-t-butyl-N-(butoxymethyl)acetanilide;
2-chloro-2'-nitro-6'-methoxy-N-(methoxymethyl)acetanilide;
2'chloro-2'-nitro-6'-(chloromethyl)-N-(ethoxymethyl)acetanilide;

Compounds of formula (I) may be prepared in accordance with the following reaction:

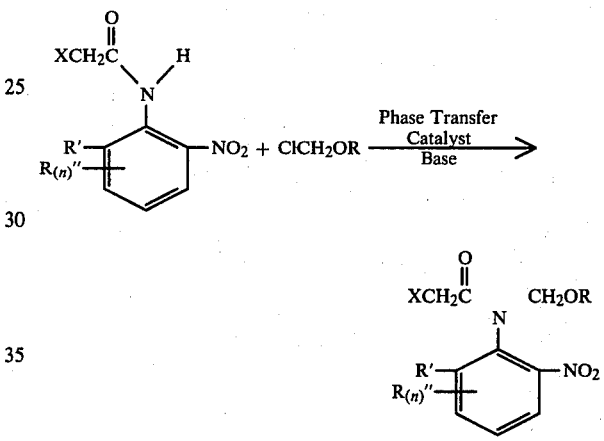

As can be seen from the above reaction, the appropriate 2-nitro-2-halo-acetanilide is reacted with a halomethyl alkyl ether in the presence of a phase transfer catalyst and strong base. The following examples illustrate the above reaction in greater detail. The examples are merely illustrative and are not intended as a limitation on the scope of the invention.

EXAMPLE 1

Preparation of 2-Chloro-2',6'-Dinitro-N-(n-Propoxymethyl)Acetanilide 2.5 g. of 2',6'dinitro-2-chloroacetanilide, 3.0 ml. of chloromethyl n-propyl ether, 150 ml of methylene chloride and 1.1 gr. of phase transfer catalyst were charged to a round-bottom flask fitted with a mechanical stirrer. To the mixture was added 100 ml. of saturated $NA_2CO_3$ in one portion. The resulting mixture was stirred for three-quarter hour at which time GLC showed no starting material indicating the reaction was complete. The product, 2-chloro-2',6'-dinitro-N-(n-propoxymethyl)acetanilide was obtained as a yellow oil, (3.1 g., yield 93%)

Anal. Calc'd. for $C_{12}H_{14}ClN_3O_6$: C, 43.45; H, 4.25; N, 12.67; Found: C, 43.41; H, 4.29; N, 12.20.

EXAMPLE 2

Preparation of 2-Chloro-2'-Nitro-6'-Methyl-N-(Ethoxymethyl)Acetanilide

To a round-bottom flask fitted with a stirrer was added 10.0 g. (0.044 moles) of 2-chloro-2'-nitro,6'methyl-acetanilide, 9.9 g. (0.1 moles) of chloromethyl ethyl ether, 1.0 g. of phase transfer catalyst and 150 ml. methylene chloride. Thereafter, aqueous sodium hydroxide (50%) was added in one portion. An exothermic reaction took place and the temperature inside the flask rose to 42° C. The contents of the flask were stirred for $\frac{1}{2}$ hour at which time GLC showed no starting material. 100 ml. of water was added to aid separation. The methylene chloride layer was separated, dried over $MgSO_4$, filtered and evaporated giving 12.9 g. of amber solid. The amber solid was recrystallized from isopropanol to give 10.9 g. of product. The product was recrystallized from heptane to give a light yellow oil, which later solidified to yield a 3.5 g. of white solid, m.p. 96°–98° C., which was identified as 2-chloro-2'-nitro-6'-methyl-N-(ethoxymethyl)acetanilide.

Anal. Calc'd. for $C_{12}H_{15}ClN_2O_4$: C, 50.27; H, 5.27; N, 9.77; Found: C, 50.27; H, 5.27; N, 9.75.

EXAMPLE 3

Preparation of 2-Chloro-2'-Nitro-N-(Ethoxymethyl) Acetanilide 4.93 g. (0.023 moles) of 2'-nitro-2-chloroacetanilide was mixed 9.9 g. (0.1 mole of chloromethyl ethyl ether in 75 ml. of methylene chloride and the mixture stirred in an ice bath. Aqueous sodium hydroxide (10%) was added in one portion and the resulting mixture stirred for one hour. 200 ml. of water was added to aid separation; the separated organic layer was washed with 2.5% NaCl, dried, filtered and stripped. The product was chromatographed on silica gel ethyl acetate/cyclohexane as eluant. 5.5 g. (62% yield) of crude product was obtained as an oil. The oil was taken up in boiling ether, hexane added to the cloud point to get a clear solution which was allowed to crystallize yielding 4.3 g. (48% yield) of white solid, m.p. 63°–65° C., which was identified as 2-chloro-2'-nitro-N-(ethoxymethyl)acetanilide.

Anal. Calc'd. for $C_{11}H_{13}ClN_2O_4$: C, 48.45; H, 4.81; N, 10.27; Found: C, 48.51; H, 4.82; N, 10.25.

EXAMPLE 4

Preparation of 2-Chloro-2'-Nitro-N-(Isobutoxymethyl)Acetanilide 6.0 g. of 2'-Nitro-2-chloroacetanilide was mixed with 6 ml. of chloromethyl isobutyl ether and 2 g. benzyltriethyl ammonium chloride (phase transfer catalyst) in 100 ml. of methylene chloride at 25° C. Thereafter, 150 ml. of 10% sodium hydroxide was added in one portion. The mixture was vigorously stirred for 30 minutes at room temperature. The organic/aqueous layers were separated and the methylene chloride layer was washed once with 2.5% sodium chloride. The sodium chloride solution was removed and the methylene chloride portion was vacuum treated to remove solvent. The residue was vacuum distilled through a Kugelrohr to give an orange oil, containing a trace of starting material. The residue was eluted through a silica gel wet column with 3:2 hexane/ether as eluant. The product was recovered as a yellow oil from the second fraction, and it distilled at 155°–165° C. (0.4 mm Hg) to give 5.1 g. (66% yield) of yellow oil identified as 2-chloro-2'-nitro-N-(isobutoxymethyl)acetanilide.

Anal. Calc'd. for $C_{13}H_{17}ClN_2O_4$: C, 51.92; H, 5.70; N, 9.31; Found: C, 52.62; H, 5.83; N, 9.21.

EXAMPLE 5

Preparation of 2-Chloro-2',6'-Dinitro-N-(Methoxymethyl)Acetanilide

To a 500 ml. stirred flask was added 3.0 g. (0.012 moles) of 2',6'-dinitro-2-chloroacetanilide, 2.5 ml. of chloromethyl methyl ether, 1.0 g. of phase transfer catalyst and 150 ml. of methylene chloride. Thereafter, 75 ml. saturated sodium carbonate solution was added in one portion and stirring continued for 50 minutes. At the end of this period, water was added to aid separation and the aqueous/organic mixture was allowed to stand overnight. The product, 2-chloro-2',6'-dinitro-N-(methoxymethyl)acetanilide, 2.9 g. m.p. 105.5°–108° C. was obtained in 80% yield.

Anal. Calc'd. for $C_{10}H_{10}ClN_2O_6$: C, 39.55; H, 3.32; N, 13.84; Found: C, 39.42; H, 3.22; N, 14.22.

In accordance with the novel aspects of the present invention many of the compounds of the foregoing formula (I) have been found to be effective as herbicides. The compounds may be used by themselves or as the active ingredient in a herbicidal composition.

As used herein, the term "herbicidal active ingredient" is understood to mean a compound of the foregoing formula (I).

Control of undesirable weed growth may be obtained by applying the herbicidal active ingredient to the plant locus which is defined herein to include the growth medium surrounding the plant, the seeds, emerging seedlings, roots, stems, leaves, flowers and other plant parts. Application to the growth medium surrounding the plants, e.g. the soil is preferred. This type of treatment is known to those skilled in the art as a pre-emergent treatment.

To illustrate the herbicidal properties of the compounds of the present invention, said compounds were tested in the following manner.

The pre-emergent test was conducted as follows:

A good grade of top soil was placed in aluminum pans and compacted to a depth of 0.95 to 1.27 cm. from the top of the pan. On the top of the soil was placed a predetermined number of seeds or vegetative propagules of various plant species. The soil required to level fill the pans after seeding or adding vegetative propagules was weighed into a pan. A known amount of the herbicidal active ingredient applied in a solvent, or as a wettable powder, and was mixed with the soil and thoroughly mixed, and thereafter used as a cover layer for prepared pans. After treatment, the pans were moved into a greenhouse bench where they were watered from below as needed to give adequate moisture for germination and growth.

As noted in Tables I and II, below, approximately 2 or 4 weeks after seeding and treating, the plants were observed to determine all deviations from the normal growth habit and the results recorded. A herbicidal rating code was used to signify the extent of inhibition or control of each species. The ratings are defined as follows:

| % Control | Rating |
| --- | --- |
| 0–24 | 0 |

-continued

| % Control | Rating |
|---|---|
| 25-49 | 1 |
| 50-74 | 2 |
| 75-100 | 3 |

R—Hemp Sesbania
S—Panicum Spp
T—Crabgrass

Results of the pre-emergent tests are summarized in Tables I and II below.

TABLE I

| Example Number | WAT* | kg h | A | B | C | D | E | F | G | H | I | J | K |
|---|---|---|---|---|---|---|---|---|---|---|---|---|---|
| 1 | 2 | 11.2 | 0 | 0 | 0 | 0 | 1 | 2 | 0 | 0 | 0 | 0 | 3 |
| 1 | 2 | 5.6 | 0 | 0 | 0 | 0 | 0 | 0 | 0 | 0 | 0 | 0 | 1 |
| 2 | 2 | 11.2 | 3 | 0 | 1 | 2 | 3 | 3 | 3 | 3 | 0 | 3 | 3 |
| 2 | 2 | 5.6 | 1 | 0 | 0 | 2 | 3 | 3 | 2 | 3 | 3 | 1 | 3 |
| 3 | 2 | 11.2 | 0 | 0 | 0 | 0 | 2 | 1 | 0 | 0 | 0 | 0 | 3 |
| 3 | 2 | 5.6 | 0 | 0 | 0 | 1 | 1 | 0 | 0 | 0 | 1 | 0 | 3 |

*Number of weeks after treatment that observations were made.

TABLE II

| Example Number | WAT* | kg h | L | M | N | O | P | B | Q | D | R | E | F | C | J | S | K | T |
|---|---|---|---|---|---|---|---|---|---|---|---|---|---|---|---|---|---|---|
| 1 | 2 | 5.6 | 0 | 0 | 0 | 0 | 0 | 0 | 0 | 0 | 0 | 0 | 0 | 0 | 0 | 0 | 1 | 1 |
| 1 | 2 | 11.2 | 0 | 0 | 0 | 0 | 0 | 0 | 0 | 0 | 0 | 0 | 0 | 0 | 0 | 1 | 0 | |
| 2 | 2 | 5.6 | 0 | 2 | 2 | 3 | 3 | 0 | 3 | 2 | 2 | 2 | 0 | 0 | 3 | 3 | 3 | 0 |
| 2 | 2 | 11.2 | 0 | 1 | 0 | 2 | 3 | 0 | 3 | 0 | 2 | 1 | 0 | 0 | 2 | 3 | 3 | 0 |
| 2 | 2 | 2.02 | 0 | 0 | 0 | 2 | 1 | 0 | 0 | 0 | 3 | 0 | 0 | 0 | 0 | 2 | 3 | 0 |
| 2 | 2 | 0.56 | 0 | 0 | 0 | 0 | 0 | 0 | 0 | 0 | 0 | 0 | 0 | 0 | 0 | 0 | 1 | 0 |
| 2 | 2 | 0.112 | 0 | 0 | 0 | 0 | 0 | 0 | 0 | 0 | 0 | 0 | 0 | 0 | 0 | 0 | 2 | 0 |
| 3 | 2 | 5.60 | 0 | 0 | 1 | 0 | 0 | 0 | 0 | 0 | 3 | 0 | 0 | 0 | 0 | 2 | 3 | 3 |
| 3 | 2 | 1.12 | 0 | 0 | 0 | 0 | 0 | 0 | 0 | 0 | 0 | 0 | 0 | 0 | 0 | 1 | 2 | 3 |
| 3 | 2 | 0.56 | 0 | 0 | 0 | 0 | 0 | 0 | 0 | 0 | 0 | 0 | 0 | 0 | 0 | 0 | 0 | 3 |
| 4 | 2 | 5.6 | 1 | 1 | 0 | 3 | 1 | 0 | 0 | 2 | 3 | 1 | 3 | 0 | 1 | 3 | 3 | 3 |
| 4 | 2 | 1.12 | 0 | 1 | 0 | 2 | 1 | 0 | 0 | 0 | 1 | 2 | 0 | 2 | 2 | 3 | 3 | |
| 4 | 2 | 0.28 | 0 | 0 | 0 | 1 | 0 | 0 | 0 | 0 | 0 | 1 | 2 | 0 | 0 | 1 | 3 | |

*Number of weeks after treatment that observations were made.

The plant species utilized in these tests are identified by letter in accordance with the following legend:
A—Canada Thistle
B—Cocklebur
C—Velvetleaf
D—Morning Glory
E—Lambsquarters
F—Smartweed
G—Nutsedge
H—Quackgrass
I—Johnson Grass
J—Downy Brome
K—Barnyard Grass
L—Soybean
M—Sugar Beet
N—Wheat
O—Rice
P—Sorghum
Q—Wild Buckwheat The post-emergent tests were conducted as follows: The herbicidal active ingredients were applied in spray form to two or three-week old specimens of various plant species. The spray, a solution of wettable powder suspension containing the appropriate rate of herbicidal active ingredient to give the desired test rate and a surfactant, was applied to the plants. The treated plants were placed in a greenhouse and approximately two or four weeks later the effects were observed and recorded. The results are shown in Tables III and IV in which the post-emergent herbicidal rating code is as follows:

| % Control | Rating |
|---|---|
| 0-24 | 0 |
| 25-49 | 1 |
| 50-74 | 2 |
| 75-99 | 3 |
| 100 | 4 |

The plant species utilized in these tests are identified by letter in accordance with the previous legend.

TABLE III

| Example Number | WAT* | kg h | A | B | C | D | E | F | G | H | I | J | K |
|---|---|---|---|---|---|---|---|---|---|---|---|---|---|
| 5 | 2 | 11.2 | 0 | 2 | 1 | 1 | 0 | 4 | 0 | 0 | 0 | 0 | 3 |
| 1 | 2 | 11.2 | 0 | 0 | 0 | 1 | 1 | 0 | 0 | 0 | 0 | 0 | 2 |
| 2 | 2 | 11.2 | 0 | 0 | 0 | 0 | 0 | 0 | 0 | 0 | 0 | 0 | 2 |
| 3 | 2 | 5.6 | 0 | 0 | 1 | 1 | 1 | 0 | 0 | 0 | 0 | 0 | 2 |
| 4 | 2 | 11.2 | 0 | 1 | 0 | 2 | 2 | 1 | 0 | 0 | 0 | 0 | 0 |

*Number of weeks after treatment that observations were made.

TABLE IV

| Example Number | WAT* | kg h | Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| 5 | 2 | 5.6 | 1 | 0 | 0 | 0 | 0 | 0 | 2 | 1 | 3 | 4 | 2 | 0 | 0 | 2 | 2 | 1 |

*Number of weeks after treatment that observations were made.

The above tables illustrate one aspect of the present invention, that is, the use of the compounds of the invention to kill or injure undesirable plants, e.g., weeds. Another aspect of the invention, however, is the use of many of the compounds of formula (I) for the regulation of desirable plant growth, especially leguminous plants such as soybeans.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth when used as a plant growth regulant, it does not include the total inhibition or killing of such plants. The present invention contemplates the use of an amount of the compounds of formula (I) as the active ingredient in a plant growth regulating composition which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to the plant locus which has been defined herein to include the growth medium surrounding the plant, the seeds, emerging seedlings, roots, stems, leaves, flowers, or other plant parts. Such application may be made directly to the plant part, or indirectly by application to the plant growth medium.

Utilizing the compounds of formula (I) as the active ingredient in a plant growth regulating composition, said compounds were found to possess plant growth regulating activity when tested in accordance with the following procedure.

A number of soybean plants, variety Williams, were grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 was used as a surfactant.

When the fifth trifoliate leaf (four to five weeks) was fully expanded, the treated plants were compared with the non-treated control plants and the observations recorded. Those observations are summarized in Table V below.

TABLE V

| Example Number | Rate (kg/h) | Observations |
|---|---|---|
| 4 | 2.8 | Stature reduction, leaf inhibition, leaf distortion, inhibition of apical development, inhibition of dry weight, severe leaf burn. |
| 4 | 0.56 | Leaf alteration, new growth, leaf inhibition, leaf alteration, slight leaf burn, inhibition of dry weight. |
| 4 | 0.112 | No response noted. |
| 1 | 2.8 | Leaf distortion, leaf alteration, leaf alteration new growth, inhibition of dry weight, slight leaf burn. |
| 1 | 0.56 | No response noted. |
| 1 | 0.112 | No response noted. |

As can be seen from the above data, the compounds of formula (I) above are especially effective at rates of about 2.8 kilograms per hectare in reducing the stature of soybean plants. At lower rates, the compounds are effective in altering the leaf morphology of the plant without reducing the plant's stature.

Thus, the above data illustrate that the compounds of the invention may be used as a herbicide or a plant growth regulant. When used as a herbicide, it is desirable that rates of application about 5.60 kilograms per hectare and above be utilized; the preferred rate is 11.2 kilograms per hectare. When used to regulate the growth of desirable plants, rates at or below 2.8 kilograms per hectare, the preferred rate is 2.8 kilograms per hectare.

In selecting the appropriate time and rate of application of the active ingredient, it will be recognized that precise rates will also be dependent upon the desired response, mode of application, plant variety, soil conditions and various other factors known to those skilled in the art. In addition, it will be recognized that single or multiple applications may be used to exert the desired response.

In the practice of the invention, the active ingredient, whether used as a herbicide or a plant growth regulant, can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, columns 3 and 4, for detailed examples of the same.

Generally, the active ingredients are applied in the form of a composition containing one or more adjuvants which aid in the application of a uniform distrubution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention, whether used as a herbicide or a plant growth regulant, generally contain from about 5 to 95 parts active ingredient, about 1 to 50 parts surface-active agent and about 4 to 94 parts solvents or inert adjuvants, all parts being by weight based on the total weight of the composition.

Typical formulations are set forth below using various of the compounds of the present invention as the active ingredient for illustrative purposes only.

Formulation 1—Solid Formulation

The following active ingredients were dissolved in an aromatic naphtha solvent extended with mineral spirits and the solution was applied to an inert solid so as to give a formulation having the following percentage of active ingredient by weight:

A 12.5% 2-chloro-2',6'-dinitro-N-(propoxymethyl)acetanilide
13.0–15.0% methylated napthalene solvent
72.5–74.5% vermiculite

B 5.0% 2-chloro-2'-nitro,6'-methyl-N-(ethoxymethyl)acetanilide
6.0% methylated napthalene solvent
89.0% attapulgite clay granules

C

50% 2-chloro-2'-nitro-N-(ethoxymethyl)acetanilide
10% aromatic naptha solvent
40% vemiculite II. Liquid Concentrate Formulation

A 35.0–37.5% 2-chloro-2'-nitro-N-(isobutoxy)acetanlide
2.5–5.0% nonylphenoxy polyoxyethylene ethanol emulsifier
57–61.5% xylene solvent

B 46.0–49.0% 2-chloro-2',6'-dinitro-N-(methoxymethyl)acetanilide
3.5–5.0% emulsifier
46.0–49.5% xylene solvent

C 69.0–75.0% of 60–69% 2-chloro-2'-nitro,6'-methyl-N-(ethoxymethyl)acetanilide
7.0% emulsifier
18.5–25.0% xylene solvent

D

95% 2-chloro-2'-nitro,6'-methyl-N-(ethoxymethyl)acetanilide
0.5% emulsifier
4.5% xylene solvent III. Emulsions

A

40% 2-chloro-2',6'-dinitro-N-(n-propoxymethyl)acetanilide
4% polyoxyethylene/polyoxypropylene block copolymer with butanol (e.g., Tergitol XH)
56% Water

B

5% 2-chloro-2'-nitro-6'-methyl-N-(ethoxymethyl)acetanilide
3.5% polyoxyethylene/polyoxypropylene block copolymer with butanol
91.5% Water IV. Wettable Powders

A 25.0% 2-chloro-2'-nitro-N-(ethoxymethyl)acetanilide
3.0% Sodium lignosulfonate
1.0% Sodium N-methyl-N-oleyl-taurate
71.0% Amorphous silica (synthetic)

B

80% 2-chloro-2-nitro-N-(isobutoxymethyl)acetanilide
1.25% Sodium dioctyl sulfosuccinate
2.75% Calcium lignosulfonate
16.00% Amorphous silica (synthetic)

C 10.00% 2-chloro-2',6'-dinitro-N-(methoxymethyl)acetanilide
3.0% Sodium lignosulfonate
1.0% Sodium N-methyl-N-oleyl-taurate
86.0% Kaolinite clay Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula $$XCH_2\overset{\overset{O}{\|}}{C}\diagdown\underset{N}{\phantom{x}}\diagup CH_2OR$$

(with phenyl ring bearing R', R(n)", and NO$_2$)

wherein X is chloro, bromo or iodo; R is C$_{1-5}$ alkyl, C$_{3-5}$ alkenyl, C$_{3-5}$ alkynyl, C$_{1-5}$ alkyl substituted by one to three C$_{1-5}$ alkoxy moieties; R' is NO$_2$; R" is C$_{1-5}$ alkyl, halogen, C$_{1-5}$ alkoxy, halo (C$_{1-5}$) alkyl, or NO$_2$; n is zero, one or two.

2. A compound according to claim 1 wherein R is C$_{1-5}$ alkyl.

3. A compound according to claim 1 wherein X is chloro.

4. A compound according to claim 1 wherein n is zero.

5. A compound according to claim 1 wherein n is one.

6. A compound according to claim 1 wherein R" is methyl, chloro, trifluoromethyl or nitro.

7. A compound according to claim 1 wherein said compound is 2-chloro-2',6'-dinitro-N-(n-propoxy)acetanilide.

8. A compound having the formula $$XCH_2\overset{\overset{O}{\|}}{C}\diagdown\underset{N}{\phantom{x}}\diagup CH_2OR$$

(with phenyl ring bearing O$_2$N— and —NO$_2$)

wherein X is chloro, bromo or iodo and R is C$_{1-5}$ alkyl.

9. A method for preventing the growth of undesirable plants which comprises applying to the plant locus a herbicidally effective amount of a compound having the formula $$XCH_2\overset{\overset{O}{\|}}{C}\diagdown\underset{N}{\phantom{x}}\diagup CH_2OR$$

(with phenyl ring bearing R', R(n)", and NO$_2$)

wherein X is chloro, bromo or iodo; R is C$_{1-5}$ alkyl, C$_{3-5}$ alkenyl, C$_{3-5}$ alkynyl, C$_{1-5}$ alkyl substituted by one to three C$_{1-5}$ alkoxy moieties; R is NO$_2$; R" is C$_{1-5}$ alkyl, halogen, C$_{1-5}$ alkoxy, halo (C$_{1-5}$) alkyl, or NO$_2$; n is zero, one or two.

10. A method according to claim 9 wherein R is C$_{1-5}$ alkyl.

11. A method according to claim 9 wherein X is chloro.

12. A method according to claim 9 wherein n is zero.

13. A method according to claim 9 wherein n is one.

14. A method according to claim 13 where R" is methyl, chloro, trifluoromethyl or nitro.

15. A method according to claim 9 wherein said compound is 2-chloro-2',6'-dinitro-N-(n-propoxy)acetanilide.

16. A method for preventing the growth of undesirable vegetation which comprises applying to the plant locus a herbicidally effective amount of a compound having the formula $$XCH_2\overset{\overset{O}{\|}}{C}\diagdown\underset{N}{\phantom{x}}\diagup CH_2OR$$

(with phenyl ring bearing O$_2$N— and —NO$_2$)

wherein X is chloro, bromo or iodo and R is C$_{1-5}$ alkyl.

17. A method of stunting the growth of desirable plants which comprises applying to the plant locus a plant growth regulating effective amount of a compound having the formula $$XCH_2\overset{\overset{O}{\|}}{C}\diagdown\underset{N}{\phantom{x}}\diagup CH_2OR$$

(with phenyl ring bearing R', R(n)", and NO$_2$)

wherein X is chloro, bromo or iodo; R is C$_{1-5}$ alkyl, C$_{3-5}$ alkenyl, C$_{3-5}$ alkynyl, C$_{1-5}$ alkyl substituted by one to three C$_{1-5}$ alkoxy moieties; R' is hydrogen, C$_{1-5}$ alkyl, C$_{1-5}$ alkoxy, halogen or NO$_2$; R" is C$_{1-5}$ alkoxy, halo (C$_{1-5}$ alkyl or NO$_2$; n is zero, one or two.

18. A method according to claim 17 wherein R is C$_{1-5}$ alkyl.

19. A method according to claim 17 wherein X is chloro.

20. A method according to claim 17 wherein R' is nitro.

21. A method according to claim 17 wherein R' is hydrogen or methyl.

22. A method according to claim 17 wherein n is zero.

23. A method according to claim 17 wherein n is one.

24. A method according to claim 23 wherein R" is methyl, chloro, trifluoromethyl or nitro.

25. A method according to claim 17 wherein said compoun is 2-chloro-2'-nitro-N-(isobutoxymethyl)acetanilide, 2-chloro-2',6'-dinitro-N-(n-propoxy)acetanilide, 2-chloro-2'-nitro-6'-methyl-N-(ethoxymethyl)acetanilide or 2-chloro-2'-nitro-N-(ethoxymethyl)acetanilide.

26. A herbicidal composition which comprises from about 1 to about 50 parts by weight surface-active agent, from about 4 to about 94 parts by weight of solvent or inert adjuvant and from about 5 to about 95 parts by weight of a compound having the formula

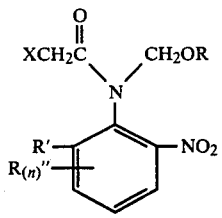

wherein X is chloro, bromo or iodo; R is $C_{1-5}$ alkyl, $C_{3-5}$ alkenyl, $C_{3-5}$ alkynyl or $C_{1-5}$ alkyl substituted by one to three $C_{1-5}$ alkoxy moieties; R' is $NO_2$; R'' is $C_{1-5}$ alkyl, halogen, $C_{1-5}$ alkoxy, halo ($C_{1-5}$) alkyl or $NO_2$; n is zero, one or two.

27. A composition according to claim 26 wherein R is $C_{1-5}$ alkyl.

28. A composition according to claim 26 wherein X is chloro.

29. A composition according to claim 26 wherein n is zero.

30. A composition according to claim 26 wherein n is one.

31. A composition according to claim 30 wherein R'' is methyl, chloro, trifluoromethyl or nitro.

32. A composition according to claim 26 wherein said compound is 2-chloro-2',6'-dinitro-N-(n-propoxy)acetanilide.

33. A herbicidal composition which comprises from about 1 to about 50 parts by weight surface-active agent, from about 4 to about 94 parts by weight of solvent or inert adjuvant and from about 5 to about 95 parts by weight of a compound having the formula

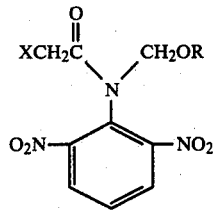

wherein X is chloro, bromo or iodo and R is $C_{1-5}$ alkyl.

* * * * *